United States Patent [19]

Kawai et al.

[11] Patent Number: 4,983,180
[45] Date of Patent: Jan. 8, 1991

[54] COATED SUTURES EXHIBITING IMPROVED KNOT SECURITY

[75] Inventors: Tatsuya Kawai; Takashi Matsuda; Michiaki Yoshimoto, all of Hiroshima, Japan

[73] Assignee: Japan Medical Supply Co., Ltd., Hiroshima, Japan

[21] Appl. No.: 317,689

[22] Filed: Mar. 1, 1989

[30] Foreign Application Priority Data

Mar. 4, 1988 [JP] Japan ................................. 65-50640

[51] Int. Cl.$^5$ ............................................. A61R 17/00
[52] U.S. Cl. ..................................... 606/230; 606/231; 606/228
[58] Field of Search ..................... 128/335.5; 606/228–231

[56] References Cited

U.S. PATENT DOCUMENTS

| | | | |
|---|---|---|---|
| 3,937,223 | 2/1976 | Roth | 604/372 |
| 3,942,532 | 3/1976 | Hunter et al. | 128/335.5 |
| 4,027,676 | 6/1977 | Mattei | 128/335.5 |
| 4,047,533 | 9/1977 | Perciaccante et al. | 128/335.5 |
| 4,105,034 | 8/1978 | Shalaby et al. | 128/335.5 |
| 4,185,637 | 1/1980 | Mattei | 128/335.5 |
| 4,201,216 | 5/1980 | Mattei | 128/335.5 |
| 4,532,929 | 8/1985 | Mattei et al. | 128/335.5 |
| 4,624,256 | 11/1986 | Messier et al. | 128/335.5 |
| 4,649,920 | 3/1987 | Rhum | 128/335.5 |
| 4,711,241 | 12/1987 | Lehmann | 128/335.5 |
| 4,791,929 | 12/1988 | Jarrett et al. | 606/228 |

FOREIGN PATENT DOCUMENTS

| | | | |
|---|---|---|---|
| 61-71058 | 11/1986 | Japan | 128/335.5 |
| 62-97648 | 6/1987 | Japan | 128/335.5 |
| 62-97649 | 6/1987 | Japan | 128/335.5 |
| 1418524 | 12/1975 | United Kingdom | 128/335.5 |
| 1583390 | 1/1981 | United Kingdom | 128/335.5 |

Primary Examiner—Randall L. Green
Assistant Examiner—Gary Jackson
Attorney, Agent, or Firm—Kramer, Brufsky & Cifelli

[57] ABSTRACT

Braided multifilament sutures exhibiting excellent tie-down performance and knot security are provided. The sutures of the invention comprise synthetic, textured braided sutures coated with a coating composition for lubricating the sutures.

4 Claims, 2 Drawing Sheets

COATED SUTURES EXHIBITING IMPROVED KNOT SECURITY

BACKGROUND OF THE INVENTION

This invention relates to surgical sutures coated with a coating material to improve fiber lubricity. More particularly, this invention relates coated surgical sutures which exhibit improved tie-down performance without a corresponding loss in knot security.

Suture materials are classified as either absorbable or nonabsorbable, and are considered to be absorbable if they disappear from the sewn tissue within a year after surgery. The most commonly used absorbable suture materials are catgut and extruded collagenous materials. More recently, absorbable sutures derived from certain synthetic polymers have been developed and used. Typical of synthetic absorbable polymers used as suture materials are glycolide homopolymer and glycolide-lactide copolymer. Synthetic absorbable materials are generally stiffer than their catgut counterpart, and synthetic absorbable sutures are therefore usually employed in a braided, multifilament construction in order to obtain desired softness and flexibility. Other materials such as polyethylene terephthalate and nylon are also employed in a braided construction as non-absorbable suture materials.

Whether absorbable or non-absorbable, synthetic braided multifilament sutures show a certain degree of unsatisfactory roughness or grabbiness in what has been termed their "tie-down" performance, i.e. the ease of sliding a knot down the suture into place. An important handling characteristic of sutures, however, is that they slide easily into place during the knotting process. Contrasted with the ease of knot placement is the ability of the knot to hold the suture, sometimes hereinafter referred to as the property of knot security. While it is desirable that surgical knots easily slide into place and tie, it is also extremely important that the knot hold for an acceptable length of time. Consequently, a number of methods have heretofore been employed in an attempt to improve these two particular characteristics of the suture.

Surface coating is the principal method which has been employed to improve tie-down performance. Commonly used coating materials include paraffin wax, beeswax and silicone oil. Other coating materials which have been used for the improvement of tie-down performance are disclosed, for example, in U.S. Pat. Nos. 4,047,533, 4,201,216, 4,185,637, 4,105,034, 3,942,532, 4,532,929, 4,027,676 and 4,711,241. In addition, the inventor of the instant invention has disclosed a coating composition comprising sucrose fatty acid ester for improving the tie-down performance of sutures in a pending patent application, U.S. Serial No. 153,996.

Although there has been some improvement in the tie-down performance of sutures including the coating compositions known in the art, the coating compositions have also resulted in a decrease in knot security. The problem of knot loosening has therefore increased, which is a particularly undesirable result.

In addition to the attempts at improving the tie-down performance of sutures, means for improving knot security have also been heretofore suggested. One method to improve knot security is to texture the yarn fibers used to form the suture. Textured yarn braided multifilament sutures are disclosed, for example, in Japanese Utility Model Application Laid-Open No. 62-97648 and No. 62-97649. These sutures are not coated and do not exhibit a tie-down performance as good as that exhibited by coated sutures.

The inventors of the present invention have found that although sutures with either improved tie-down performance or knot security are known in the surgical arts, braided multifilament sutures having the aforementioned two characteristics are not presently known.

SUMMARY OF THE INVENTION

The object of the present invention is to provide sutures which simultaneously exhibit improved tie-down performance and maintain sufficient knot security.

In the present invention the aforementioned object is accomplished by coating the surface of textured yarn braided sutures with a lubricating material.

Coating the surfaces of braided sutures formed from non-textured yarns or fibers to improve tie-down performance will result in a decrease in the knot security property of the sutures. On the other hand, the inventors herein have surprisingly found that coating the surfaces of textured yarn or fiber braided sutures with a properly selected coating composition results not only in the maintenance of knot security, but also can result in better knot security than that exhibited by uncoated textured sutures.

BRIEF DESCRIPTION OF THE DRAWINGS

The features and characteristics of the fiber yarn or construction, as well as the methods for testing suture tie-down performance and knot security are more readily understood by reference to the drawings.

DETAILED DESCRIPTION OF THE INVENTION

Figure 1:
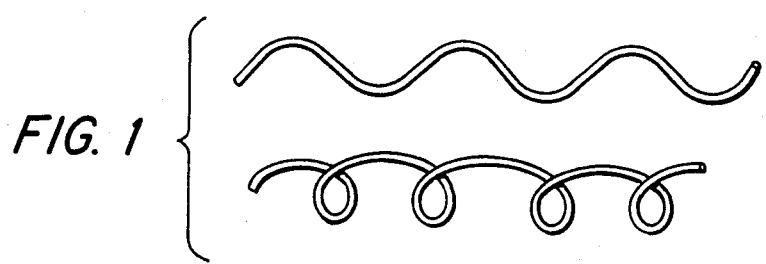
FIG. 1 is an enlarged view of a suture fiber used to form the textured yarn.

The textured yarns of the present invention are braided multifilament yarns, in which the fibers have two-dimensional or three-dimensional crimps, as illustrated in FIG.1.

There are a number of methods which can be employed to introduce the crimps into the fibers. Examples include the twisting-untwisting method, false twist method, knit-deknit method, stuffing box method, crimping gear method and friction method. Each of these methods is well known to persons skilled in the relevant art, and can readily be performed by such persons.

The present invention can be applied to both absorbable sutures and/or non-absorbable sutures.

When absorbable sutures are to be employed, it is preferable to use as the suture material an aliphatic polyester. Such aliphatic polyesters can be obtained, for example, by polymerizing materials such as lactide, glycolide,β-hydroxybutylcarboxylic acid, β-propiolactone, 7-butyrolactone, 8-valerolactone, ε-caprolactone and chitin.

When non-absorbable sutures are used, it is preferable to use as the suture material an aromatic polyester or a nylon. Particularly preferred is polyethylene terephthalate.

Sucrose fatty acid ester, beeswax, polyoxyethylene-polyoxyproxylene glycol, mixtures of stearic acid and copolymers of glycolide and lactide having a low degree of polymerization, gelatin, silicone, paraffin wax and polytetrafluorethylene are examples of suitable coating materials to be used for improving suture tie-down performance in accordance with the present invention. Among above named coating materials, sucrose fatty acid ester, beeswax, mixtures of stearic acid, copolymers of glycolide and lactide having a low degree of polymerization, and paraffin wax are particularly preferred, since sutures coated with these materials also exhibit excellent knot security.

In a preferred embodiment of the present invention, the coating is applied to the suture surfaces as a liquid coating composition which is then solidified. The liquid comprises a solution of the coating material dissolved in a volatile solvent, and solidification is accomplished by volatizing the solvent. The coating solution may also be applied to the sutures by any suitable process, such as dipping the sutures into the solution, spraying the liquid solution on the sutures or moving the sutures past a brush wetted with the coating solution. When a readily meltable coating material is used, the coating material may be heated until it melts and then applied to the sutures by any of the methods described above. In the latter case, solidification of the coating material takes place by cooling.

In place of liquiform coating composition, the composition may be comprised of solid which is applied to the suture by passing the suture over or between solid blocks of the coating composition which is transferred to the surface of the suture by a rubbing action. One coating procedure may be sufficient, however, such process may be carried out two or more times.

The improved tie-down properties and knot security of the sutures of the present invention can be shown qualitatively and/or organoleptically by comparing the feel of the coated and the uncoated sutures during the tie-down procedure. Furthermore, the improvement can also be shown quantitatively by employing the test illustrated in FIG. 2.

Figure 3:
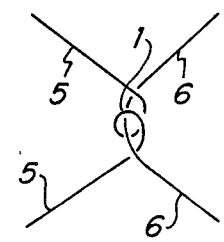
FIG. 3 is a detailed illustration of the formation of the knot illustrated in FIG.2.

To perform the tie-down measurement, two sutures, 5 and 6, are intertwined as shown in FIG. 3, with one of them fixed at Point A and Point B. One end of the other suture is passed around pulley 3 and attached to weight 4 while placing force (F) on the other end. The weight which will be used to provide tension preferably weighs between about 50 and about 100 grams.

Figure 2:
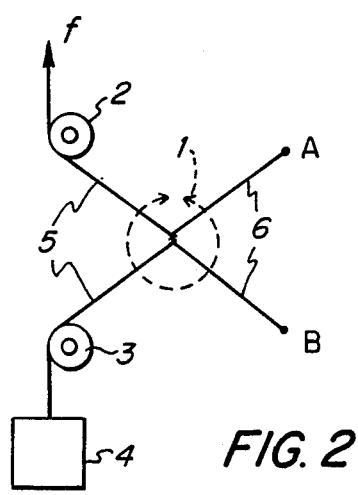
FIG. 2 is a frontal view of the test device for determining tie-down performance.
Figure 4:
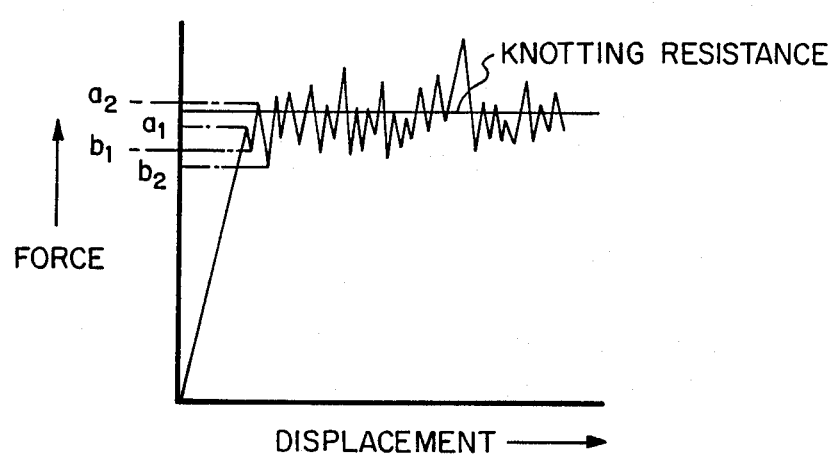
FIG. 4 is a representation of a typical chart of an oscillographic recorder for a knot security test.

Force (knotting resistance) and fluctuations (roughness value) are measured with the device shown in FIG. 2 to evaluate tie-down performance. FIG. 4 is a representation of a typical trace of tension fluctuation measured with the device illustrated in FIG. 2.

The difference in the level between a1 and b1 is the roughness value. The final roughness value measured is the roughness average value which is the difference of the maximum value and the minimum value next to each other; for example, $(a1 - b1) + \ldots + (an - bn)/n$. In other words, the lower the knotting resistance is, the smaller the force required, the smaller the roughness value is and the smoother the tie-down accomplished.

Figure 5A:
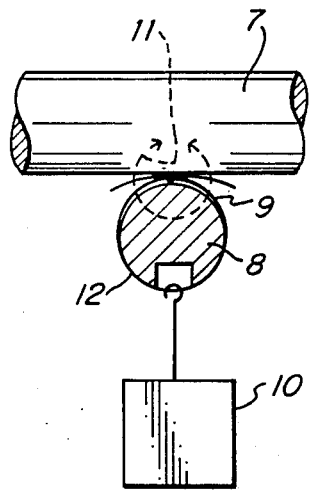
FIG. 5 is a partial sectional view (a) and a partial frontal view (b) of the test device used for determining knot security.
Figure 5B:
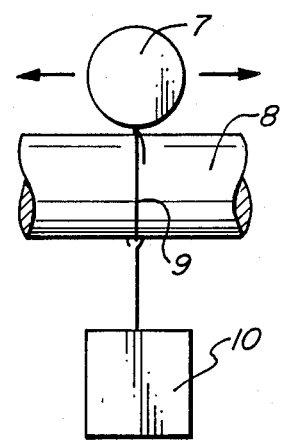

The knot securing or knot holding property of the sutures may also be determined quantitatively by a test device illustrated in FIG. 5, wherein (a) is a partial sectional view of the device and (b) is a frontal view of the device. The test is performed as follows.

Figure 6:
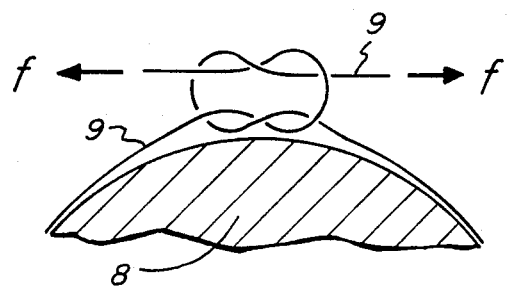
FIG. 6 is a detailed illustration of the manner for knotting sutures illustrated in FIG. 5.

First, a suture 9 is wound around a holding bar 8 having a groove 12 parallel to the axis. The suture is tied down in a manner depicted in FIG. 6. (FIG. 6 is an enlarged view of 11 in FIG. 5(a)). The suture is then subjected to a constant force F at each of the ends of the suture to firmly knot the suture. A weight 10 is then hooked onto the suture as shown in FIGS. 5(a) and (b), at a space created by the groove 12. Thereafter, a pressor bar 7, which crosses with the holding bar 8, is moved back and forth in a direction parallel to the holding bar 8, and the number of reciprocating cycles required to completely loosen the knot is counted.

In the following examples, the test procedures were each performed five times. The reported values represent the averages of five trials per test specimen.

EXAMPLE 1

Crimping was introduced into multifilaments composed of glycolide homopolymer by a method of twisting and untwisting the multifilament. That is, the crimped multifilaments were obtained by untwisting already twisted multifilament after heat treatment of the twisted multifilaments for fixing the twist. U.S.P. size 3 −0 textured sutures were prepared by braiding the multifilaments. For the purpose of comparison, non-textured sutures having no crimp were also prepared.

Three different kinds of coating materials, sucrose fatty acid ester, beeswax and silicone were then applied to each of the test sutures surfaces. The coating of the sutures with the lubricating material was accomplished as follows:

(1) Sucrose fatty acid ester (Coat A).

50 grams of sucrose fatty acid ester were mixed with one liter of ethyl acetate. The mixture was then placed in a 60° C. water bath to dissolve the sucrose fatty acid ester. In this example, a fatty acid composed of stearic acid, palmitic acid and acetic acid reacted with sucrose was used as the sucrose fatty acid ester. The hydroxyl value of the fatty acid ester was less than 20. Sutures were then dipped into the coating solution for 30 seconds, while the solution was maintained in the water bath at 60° C. Upon removal from the coating solution, the sutures were dried for 30 minutes under −760 mm Hg at 60° C. The sutures were then analyzed for sucrose fatty acid ester absorption on the basis of weight change. Sucrose fatty acid ester absorption was found to be about 5%.

(2) Beeswax (Coat B)

200 grams of beeswax were dissolved in one liter of diethyl ether solvent at room temperatures. The sutures were then placed in the beeswax solution. Upon removal from the beeswax solution, the sutures were wiped lightly with a wet gauze to remove the excess solution. The sutures were then dried for 60 minutes under atmospheric conditions of −760 mm Hg and a temperature of 60° C. The amount of beeswax pick-up was determined to be about 10%.

(3) Silicone (Coat C)

Silicone oil was sprayed onto the sutures from a distance of about 10 cm. Silicone pick-up was about 30%. Textured and non-textured sutures coated with the three different coating compositions were prepared as described above, and then tested for tie-down performance and knot security. Uncoated sutures were also tested for tie-down performance and knot security for comparative purposes. Tie-down performance was tested using both 50 gm and 100 gm weights. The average results for five trials of each of the test specimens are set forth in Table 1.

TABLE 1

|  |  | Tie-down performance | | | | Knot Security |
|---|---|---|---|---|---|---|
|  |  | 50 g load | | 100 g load | | |
|  |  | K.R. | R.V. | K.R. | R.V. | |
| Textured Suture | Uncoated | 220 g | 112 g | 410 g | 123 g | 33.4 times |
|  | Coat A | 180 | 10 | 330 | 20 | 57.4 |
|  | Coat B | 180 | 11 | 280 | 26 | 46.1 |
|  | Coat C | 200 | 13 | 360 | 17 | 35.2 |
| Non-textured suture | Uncoated | 230 | 108 | 400 | 129 | 13.8 |
|  | Coat A | 190 | 10 | 350 | 22 | 10.9 |
|  | Coat B | 200 | 10 | 300 | 23 | 9.8 |
|  | Coat C | 180 | 12 | 340 | 18 | 6.1 |

K.R. = Knotting Resistance
R.V. = Roughness Value

As shown by the results set forth in Table 1, and as expected from information available in the art, tie-down performance of sutures is significantly improved when the sutures are coated with a lubricating material. However, as also shown from the data, knot security decreases when non-textured sutures are covered with such a lubricating material.

On the other hand, it has surprisingly been found that the textured sutures exhibit improvement in knot security, even when coated with a lubricating coating. The present invention thus provides sutures which exhibit both excellent tie-down performance and knot security. With the present invention in practice, sutures having one-third less or even preferably one-fifth less roughness value of tie-down performance than uncoated sutures which also have equivalent or better knot security than that of uncoated textured suture, are obtained.

What is claimed is:

1. A suture exhibiting an improved tie-down performance and maintaining good knot security when tied, comprising braided synthetic fibrous sutures coated with a coating composition for lubricating the suture, the fibers of the suture having crimps for providing texture to the suture.

2. A suture according to claim 1 wherein said suture exhibits one-third less of a roughness value of tie-down performance than that of an uncoated suture and also exhibits an equivalent or improved knot security when tied in place than that for an uncoated, textured suture.

3. A suture according to claim 1 wherein said coating composition is selected from the group consisting of sucrose fatty acid ester, beeswax, a mixture of stearic acid and copolymers of glycolide and lactide having a low degree of polymerization and paraffin wax.

4. A suture according to claim 1 wherein said suture comprises a synthetic polymer selected from the group consisting of polyglycolide, copolymers of glycolide and lactide, aromatic polyester, and nylon.

* * * * *